(12) United States Patent
Caracci et al.

(10) Patent No.: US 7,576,333 B2
(45) Date of Patent: Aug. 18, 2009

(54) OPTICAL INTERROGATION SYSTEM AND METHOD FOR USING SAME

(75) Inventors: Stephen J. Caracci, Elmira, NY (US); Robert A. Modavis, Painted Post, NY (US); David A. Pastel, Horseheads, NY (US); Qi Wu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 11/888,495

(22) Filed: Aug. 1, 2007

(65) Prior Publication Data

US 2009/0032690 A1 Feb. 5, 2009

(51) Int. Cl.
*G01J 1/58* (2006.01)
*G01N 33/53* (2006.01)
*G01N 21/62* (2006.01)
*C12Q 1/04* (2006.01)

(52) U.S. Cl. .................. 250/458.1; 250/459.1; 435/7.1; 435/34; 436/171

(58) Field of Classification Search ......................... 250/227.14–227.24; 356/445, 600, 601; 435/7.1, 435/287.2, 7.9, 34, 283.1; 436/167–172
See application file for complete search history.

(56) References Cited

U.S. PATENT DOCUMENTS

| | | | | |
|---|---|---|---|---|
| 3,176,306 A | 3/1965 | Burns | ........................... | 346/33 |
| 4,314,763 A | 2/1982 | Steigmeier et al. | .......... | 356/237 |
| 4,815,843 A | 3/1989 | Tiefenthaler et al. | ........ | 356/128 |
| 4,818,886 A * | 4/1989 | Drucker | ...................... | 250/566 |
| 2003/0138020 A1* | 7/2003 | Chen | ........................... | 372/75 |
| 2004/0263841 A1* | 12/2004 | Caracci et al. | .............. | 356/300 |
| 2005/0227374 A1 | 10/2005 | Cunningham | ............... | 436/518 |
| 2006/0141527 A1 | 6/2006 | Caracci et al. | ............... | 435/7.1 |
| 2007/0020689 A1 | 1/2007 | Caracci et al. | ............... | 435/7.1 |

FOREIGN PATENT DOCUMENTS

WO  WO 2006/103663  10/2006

OTHER PUBLICATIONS

U.S. Appl. No. 60/781,397, filed Mar. 10, 2006, J. Gollier et al.
U.S. Appl. No. 11/711,207, filed Feb. 27, 2007, J. Gollier et al.
Ph.M. Nellen et al.,"Integrated Optical Input Grating Couplers as Biochemical Sensors", Sensors and Actuators, vol. 15, 1988, pp. 285-295.
J.P. Golden et al., "A Comparison of Imaging Methods For Use In An Array Biosensor", Biosensors and Bioelectronics, vol. 17, 2002, pp. 719-725.

(Continued)

*Primary Examiner*—Georgia Y Epps
*Assistant Examiner*—Jennifer Bennett
(74) *Attorney, Agent, or Firm*—Thomas R. Beall; William J. Tucker (57) ABSTRACT

An optical interrogation system and a method are described herein that enable the interrogation of one or more biosensors which can be located within the wells of a microplate. In one embodiment, the optical interrogation system has a tunable laser, N-fiber launches, N-lenses and N-detectors that are set-up to interrogate N-biosensors. In another embodiment, the optical interrogation system has a tunable laser, N-fiber launches, N+1 lenses and N-detectors that are set-up to interrogate N-biosensors.

16 Claims, 10 Drawing Sheets

OTHER PUBLICATIONS

P.Y. Li et al., "A New Method For Label-Free Imaging Of Biomolecular Interactions", Sensors and Actuators B, vol. 99, 2004, pp. 6-13.

C.E. Jordan et al., "Surface Plasmon Resonance Imaging Measurements of DNA Hybridization Adsorption and Streptavidin/DNA Multilayer Formation at Chemically Modified Gold Surfaces", Anal. Chem, 1997, vol. 69, pp. 4939-4947.

Z.H. Wang et al., "A Label-Free Multisensing Immunosensor Based on Imaging Ellipsometry", Anal. Chem., 2003, vol. 75, pp. 6119-6123.

J.P. Landry et al., "Label-Free Detection of Microarrays of Biomolecules by Oblique-Incidence Reflectivity Difference Microscopy", Optics Letters, Mar. 15, 2004, vol. 29, No. 6, pp. 581-583.

M. Piliarik et al., "A New Surface Plasmon Resonance Sensor For High-Throughput Screening Applications", Biosensor and Bioelectronics, vol. 20, 2005, pp. 2104-2110.

G.J. Wegner et al., "Characterization and Optimization of Peptide Arrays for the Study of Epitope—Antibody Interactions Using Surface Plasmon Resonance Imaging", Anal. Chem., 2002, vol. 74, pp. 5161-5168.

G.J. Wegner et al., "Real-Time Surface Plasmon Resonance Imaging Measurements for the Multiplexed Determination of Protein Adsorption/Desorption Kinetics and Surface Enzymatic Reactions on Peptide Microarrays", Anal. Chem., 2004, vol. 76, pp. 5677-5684.

J.M. Jung et al., "A Fusion Protein Expression Analysis Using Surface Plasmon Resonance Imaging", Analytical Biochemistry, vol. 330, 2004, pp. 251-256.

V. Kanda et al., "Label-Free Reading of Microarray-Based Immunoassays With Surface Plasmon Resonance Imaging", Anal. Chem., 2004, vol. 76, pp. 7257-7262.

C.R. Mace et al., "Theoretical and Experimental Analysis of Arrayed Imaging Reflectometry as a Sensitive Proteomics Technique", Anal. Chem., 2006, vol. 78, pp. 5578-5583.

K. Tiefenthaler et al., "Integrated Optical Switches and Gas Sensors", Optics Letters, Apr. 1984, vol. 10, No. 4, pp. 137-139.

* cited by examiner

OPTICAL INTERROGATION SYSTEM AND METHOD FOR USING SAME

TECHNICAL FIELD

The present invention relates to an optical interrogation system and a method for interrogating one or more biosensors which can be located within the wells of a microplate.

BACKGROUND

Today non-contact optical sensor technology is used in many areas of biological research to help perform increasingly sensitive and time-constrained assays. In one application, an optical interrogation system can be used to monitor changes in the refractive index or variations in the optical response/optical resonance of an optical biosensor as a biological substance is brought into a sensing region of the biosensor. The presence of the biological substance alters the optical resonance of the biosensor when it causes a biochemical interaction like material binding, adsorption etc. . . . It is this alteration of the optical resonance that enables one to use the biosensor to directly monitor a biological event in label-free assays. Examples of biosensors include surface plasmon resonance (SPR) sensors and waveguide grating coupler (WGC) sensors. A detailed discussion about the structure and function of the WGC sensor is provided in the following documents:

- U.S. Pat. No. 4,815,843 entitled "Optical Sensor for Selective Detection of Substances and/or for the Detection of Refractive Index Changes in Gaseous, Liquid, Solid and Porous Samples".
- K. Tiefenthaler et al. "Integrated Optical Switches and Gas Sensors" Opt. Lett. 10, No. 4, April 1984, pp. 137-139.
- Ph. M. Nellen, K Tiefenthaler, W. Lukosz, "Integrated Optical Input Grating Couplers as Biochemical Sensors" Sensors and Actuators, 15, 273 (1988).

The contents of these documents are incorporated by reference herein.

The optical interrogation system used today to interrogate the biosensor can take many forms, and two of the more general forms are briefly described next. In one case, the optical interrogation system delivers a single-wavelength, high-angular content optical beam to the biosensor, and the output beam received from the biosensor provides some information about the angular response of the biosensor. This type of optical interrogation system is commonly referred to as an angular interrogation system since angular detection is employed to locate a dominant angle in the output beam which is indicative of the particular optical response/optical resonance of the biosensor. In another case, the optical interrogation system delivers a collimated optical beam containing a range of wavelengths to the biosensor, the output beam received from the biosensor provides some information about the wavelength response of the biosensor. This type of optical interrogation system is commonly referred to as a spectral interrogation system since the spectrum of the output beam is analyzed to locate the resonant wavelength in the output beam which is indicative of the particular optical response/optical resonance of the biosensor.

These types of optical interrogation systems work relatively well but there is still a desire to try and design a new and improved optical interrogation system that can be used to interrogate a biosensor to determine if a biomolecular binding event (e.g., binding of a drug to a protein) or if some other event occurred on a surface of the biosensor. Accordingly, there has been and is a need for a new and improved optical interrogation system that can be used to interrogate a biosensor. This need and other needs have been addressed by the optical interrogation system and interrogation method of the present invention.

SUMMARY

The present invention includes an optical interrogation system and a method for using the same to interrogate one or more biosensors. In this embodiment, the optical interrogation system includes: (a) a tunable laser for generating an optical beam; (b) a first fiber launch for receiving the optical beam generated by the tunable laser and then outputting a first optical beam; (c) a first lens for collimating the first optical beam outputted from the first fiber launch such that the collimated optical beam illuminates a first biosensor; (d) the first lens for receiving a first reflected optical beam from the first biosensor; (e) a first detector, located ahead of or past a focal point of said first lens, for receiving a first defocused optical beam from the first lens, and (f) a data processing device for receiving and processing one or more intensity spot patterns associated with the first defocused optical beam received at the first detector. In a preferred embodiment, this optical interrogation system would have the tunable laser, N-fiber launches, N-lenses and N-detectors that are configured to interrogate N-biosensors.

In another aspect, the present invention includes an optical interrogation system and a method for using the same to interrogate one or more biosensors. In this embodiment, the optical interrogation system includes: (a) a tunable laser for emitting an optical beam; (b) a first fiber launch for receiving the optical beam emitted from the tunable laser and then outputting a first optical beam; (c) a first lens for collimating the first optical beam outputted from the first fiber launch such that the collimated first optical beam illuminates a first biosensor; (d) a second lens for receiving a first reflected optical beam from the first biosensor; (e) a first detector for receiving the first reflected optical beam from the second lens; and (f) a data processing device for receiving and processing one or more images associated with the first reflected optical beam received at the first detector. In a preferred embodiment, this optical interrogation system would have the tunable laser, N-fiber launches, N+1 lenses and N-detectors that are configured to interrogate N-biosensors.

Additional aspects of the invention will be set forth, in part, in the detailed description, figures and any claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF THE DRAWINGS

A more complete understanding of the present invention may be had by reference to the following detailed description when taken in conjunction with the accompanying drawings wherein.

DETAILED DESCRIPTION

Figure 1:
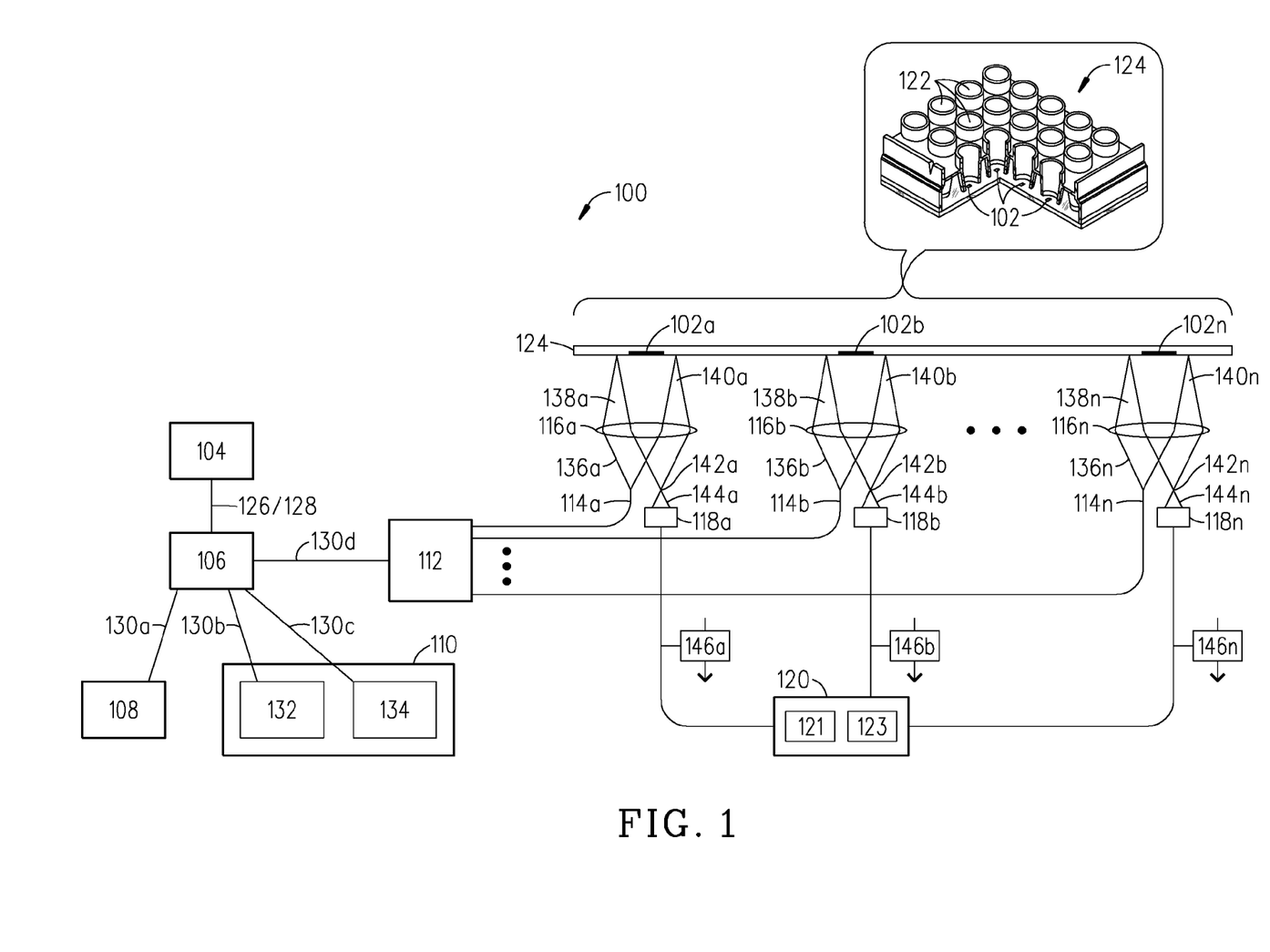
FIG. 1 is a block diagram of an exemplary optical interrogation system which is configured to interrogate one or more biosensors in accordance with a first embodiment of the present invention.

Referring to FIG. 1, there is a block diagram illustrating the basic components of an exemplary optical interrogation system 100 which is configured to interrogate one or more biosensors 102a, 102b . . . 102n in accordance with a first embodiment of the present invention. The exemplary optical interrogation system 100 includes a tunable laser 104, a 1×4 splitter 106, a power tracking device 108, a wavelength tracking device 110, a 1×N splitter 112, N-fiber launches 114a, 114b . . . 114n (e.g., N-single mode optical fibers 114a, 114b . . . 114n), N-lenses 116a, 116b . . . 116n (e.g., N-doublets 116a, 116b . . . 116n) and N-detectors 118a, 118b . . . 118n (e.g., N-dual detectors 118a, 118b . . . 118n) and a data processing device 120 (e.g., computer 120). In this example, the biosensors 102a, 102b . . . 102n are shown located within the wells 122 of a microplate 124 (note: the microplate 124 can have any number of wells 122 such as for example 96-wells, 384-wells and 1536-wells). For a detailed discussion about an exemplary microplate 124, reference is made to the co-assigned U.S. patent application Service Ser. No. 11/489,173 (the contents of which are incorporated by reference herein).

The tunable laser 104 (e.g., swept wavelength tunable laser 104) emits an optical beam 126 which has a predetermined sequence of distinct wavelengths over a predetermined time period. For instance, the tunable laser 104 can have a tuning range where the emitted optical beam 126 sequences through 840 nm to 852 nm at 12 nm increments without mode hop at a tuning speed of 0.1 nm/sec to 300 nm/sec. The tunable laser 104 is shown emitting the optical beam 126 into a fiber optic cable 128 which is connected to the 1×4 splitter 106. In this example, the 1×4 splitter 106 receives the optical beam 126 and inputs the optical beam 126 into four separate fiber optic cables 130a, 130b, 130c and 130d.

The first fiber optic cable 130a interfaces with the power tracking device 108 which functions to track the changing power of the optical beam 126 emitted from the tunable laser 104 (note: the power of the tunable laser 104 varies as it changes the wavelength of the optical beam 126). The power tracking device 108 monitors this changing power which is used by the data processing device 120 as a power reference to remove the effect of power variations in the output of the spectra from the interrogated biosensor(s) 102a, 102b . . . 102n.

The second and third fiber optic cables 130b and 130c interface with the wavelength tracking device 110 which functions to track the changing wavelengths of the optical beam 126, emitted from the tunable laser 104. In one embodiment, the wavelength tracking device 114 includes a fiber Mach-Zehnder interferometer 132 and an athermalized etalon 134. The fiber Mach-Zehnder interferometer 132 is used to decode the instantaneous wavelength of the optical beam 126, to a very high resolution while operating the tunable laser 104. The athermalized etalon 134 is used to provide an accurate reference of the wavelength of the optical beam 126 while operating the tunable laser 104. An alternative embodiment for tracking the changing wavelengths of the optical beam 126 that could also be used herein was discussed in a co-assigned U.S. patent application Ser. No. 11/711,207— the contents of which are hereby incorporated by reference herein).

The fourth fiber optic cable 130d interfaces with the 1×N splitter 112 which interfaces with N-fiber launches 114a, 114b . . . 114n (e.g., N single-mode fibers 114a, 114b . . . 114n) where each fiber launch 114a, 114b . . . 114n outputs an optical beam 136a, 136b . . . 136n towards a corresponding lens 116a, 116b . . . 116n (e.g., collimating/imaging doublet 116a, 116b . . . 116n). The lenses 116a, 116b . . . 116n respectively collimate the optical beams 136a, 136b . . . 136n and direct the collimated optical beams 138a, 138b . . . 138n to illuminate and preferably overfill the corresponding biosensors 102a, 102b . . . 102n. In addition, the lenses 116a, 116b . . . 116n respectively receive the optical beams 140a, 140b . . . 140n that are reflected from the corresponding biosensors 102a, 102b . . . 102n. The lenses 116a, 116b . . . 116n respectively focus the reflected optical beams 140a, 140b . . . 140n which are then allowed to diverge beyond the focal points 142a, 142b . . . 142c of the lenses 116a, 116b . . . 116n before the defocused optical beams 144a, 144b . . . 144n are incident upon the corresponding detectors 118a, 118b . . . 118n. Alternatively, the detectors 118a, 118b . . . 118n could be placed ahead of the focal points 142a, 142b . . . 142n so they can receive the defocused optical beams 144a, 144b . . . 144n.

The detectors 118a, 118b . . . 118n generate a sequence of intensity spot patterns 146a, 146b . . . 146n from the respective biosensors 102a, 102b . . . 102n where each of the intensity spot patterns 146a, 146b . . . 146n corresponds with one of the distinct wavelengths of the optical beam 126 that was emitted from the tunable laser 104. For instance, detector 118a generates a sequence of intensity spot patterns 146a of the illuminated biosensor 102a where each intensity spot pattern 146a corresponds with one of the distinct wavelengths of the optical beam 126 (and optical beam 136a) that was emitted from the tunable laser 104 (and the fiber launch 114a). Lastly, the data processing device 120 (e.g., computer 120) receives the collected intensity spot patterns 146a, 146b . . . 146n and has a processor 121 which uses instructions accessed from memory 123 to process the collected images 146a, 146b . . . 146n to determine for example whether or not there was a biochemical interaction or some other event that occurred on one or more of the biosensors 102a, 102b . . . 102n.

In the next section, an experimental optical interrogation system 100 is described which is configured to be a dual defocused optical interrogation system 100. This discussion is followed by a discussion about the characterization of the experimental defocused dual optical interrogation system 100 in terms of measuring source/detector noise, lateral and angular sensitivity, parasitic fringes and wavelength noise. In addition to these measurements, a modification to the biosensors 102a. 102b . . . 102n was made and experimentally evaluated and found to have enhanced the performance of the experimental defocused dual optical interrogation system 100. Finally, the results of the measurements that are associated with the testing of the experimental defocused dual optical interrogation system 100 are summarized.

Experimental Optical Interrogation System 100

Figure 2:
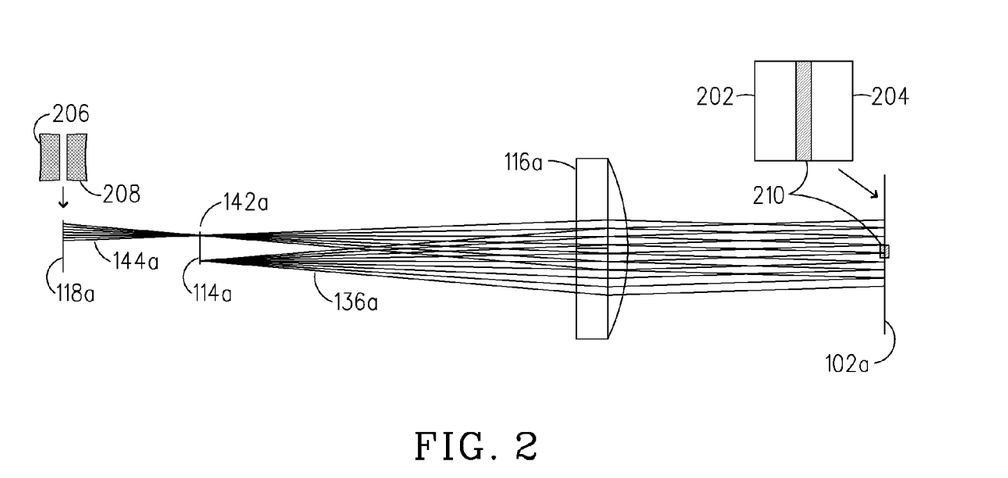
FIGS. 2-9 illustrate a block diagram, graphs and photos which are used to help explain the results of testing an exemplary optical interrogation system which is configured in accordance with the first embodiment of the present invention.

A defocused dual optical interrogation system 100 has been made and tested which had a configuration similar to the system illustrated FIG. 1 except that the detectors 118a, 8b . . . 118n are dual detectors 118a, 118b . . . 118n where each are used to receive intensity spot patterns of both a sample region 202 and a reference region 204 on the respective biosensors 102a, 102b . . . 102n (see FIG. 2). The light source for the experimental defocused dual optical interrogation system 100 was a New Focus (6300 Velocity) 840 nm tunable laser 104 which was coupled to a single-mode fiber output 128. The usable laser tuning range was approximately 12 nm between 840 nm-852 nm. The output from the tunable laser 104 was split by a 1×4 splitter 106 and input into four single-mode fibers 130a, 130b, 130c and 130d. The first output is sent to a power tracking device 108 which was used to monitor the power of the tunable laser 104. The second output was coupled to a fiber Mach-Zehnder interferometer 132 which had an 8 pm period, while the third output was sent to a temperature stable (ULE) etalon 134 which had a free spectral range of 188 pm. The two devices 132 and 134 where used to monitor the wavelength of the optical beam 126 generated by the tunable laser 104. The fourth single-mode output was coupled to a polarization scrambler (Fiberpro PS 3000) which was in turn coupled to the N-fiber launches 114a, 114b . . . 114n where the corresponding optical beams 136a, 136b . . . 136n exit at the end of a flat polished ferrules (note: the polarization scrambler was not shown in FIG. 1). The emitted light 136a, 136b . . . 136n was respectively collimated by doublets 116a, 116b . . . 116n (Thorlabs part #AC127-019-B) which had 19 mm focal lengths. The doublets 116a, 116b . . . 116n produced beams 4.1 mm in diameter (to the $1/e^2$ points) which substantially overfilled the 2×2 mm biosensors 102a, 102b . . . 102n. The biosensors 102a, 102b . . . 102n had single gratings in which the "left half" and the "right half" respectively corresponded to the signal and reference regions 202 and 204 (see FIG. 2 which illustrates one doublet 116a, one biosensor 102a and one dual detector 118a). The light 140a, 140b . . . 140n reflected by both "halves" of the biosensors 102a, 102b . . . 102n was focused by the respective doublets 116a, 116b . . . 116n and then allowed to diverge beyond the focal points 142a, 142b . . . 142n of the doublets 116a, 116b . . . 116c before the expanded defocused beams 144a, 144b . . . 144n where incident upon the dual detectors 118a, 118b . . . 118n (Hamamatsu detector 118). In this setup, the vertical distance between the fiber launches 114a, 114b . . . 114n and intensity spot pattern planes was 4 mm, between the fiber launches 114a, 114b . . . 114n and lenses 116a, 116b . . . 116n was 19 mm and between the lenses 116a, 116b . . . 116n and the microplate 1024 was 12 mm.

As can be seen in FIG. 2, the light 140a reflected from the sensor and references regions 202 and 204 on the biosensor 102a respectively illuminated specific regions 206 and 208 on the dual detector 118a. For a detailed discussion about an exemplary biosensor 102 which has a sample region 202 (signal spectra 302) and a reference region 204 (reference spectra 304) reference is made to co-assigned U.S. patent application Ser. No. 10/027,509 filed on Dec. 29, 2004 and entitled "Method for Creating a Reference Region and a Sample Region on a Biosensor and the Resulting Biosensor". The contents of this particular document are hereby incorporated by reference herein.

Figure 3:
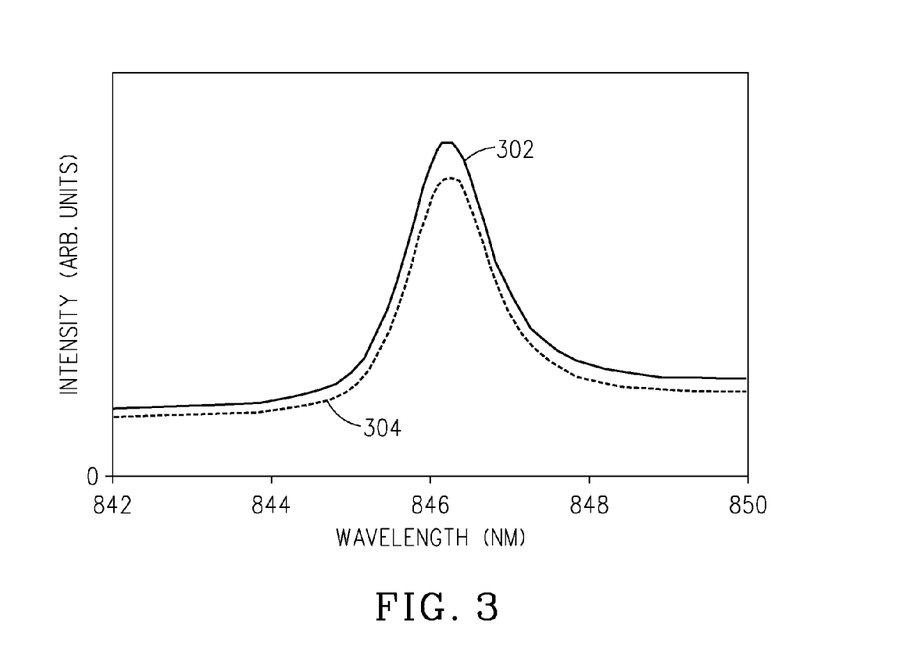

In this scheme, the sample and reference region 202 and 204 have nominally the same resonance wavelength (but are spatially resolved by the dual detector 118a) as has been illustrated in FIG. 3. The location of the resonance feature, $\lambda_c$, for the signal spectra 302 (sample region 202) and the reference spectra 304 (reference region 204) was determined using a $1^{st}$ moment centroid algorithm:

$$\lambda_c = \sum_{i=1}^{N} \frac{\lambda_i (P_i - P_{th})}{(P_i - P_{th})}$$

where $\lambda_i$, $P_i$ are the wavelengths and corresponding power levels above the threshold power, $P_{th}$.

The various sensitivity measurements (translation measurements, angular measurements) discussed below are referenced measurements, i.e. they where made by calculating the difference between the resonant wavelengths of the signal and reference spectra 302 and 304. Plus, the translation measurements where made by moving the microplate 124 in the x-direction (parallel to the grating lines on the biosensors 102a, 102b . . . 102n) and y-direction (perpendicular to the grating lines on the biosensors 102a, 102b . . . 102n) with a Newport controller (ESP 300) and linear stages. This allowed precise automated measurements to be made of the biosensors 102a, 102b . . . 102b located within the wells 122 of the microplate 124. And, the angular measurements where made manually by using a tip-tilt stage attached to the microplate 124. The precision of the angular measurements in this particular set-up was on the order of 100 μRd.

Measurements and Calculations

I. Source/Detector Noise.

Figure 4:
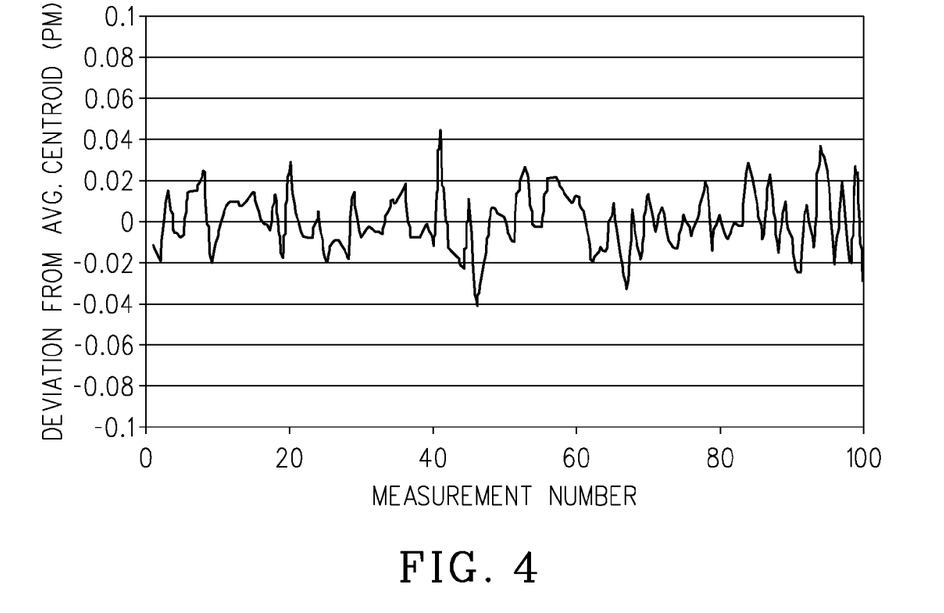
Figure 5A:
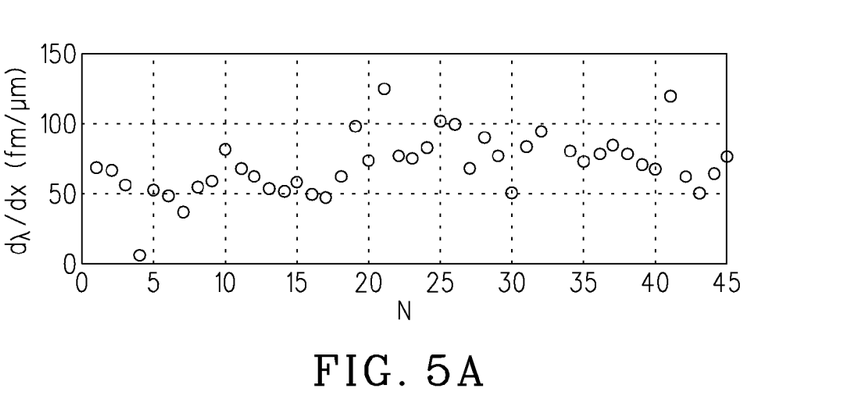
Figure 5B:
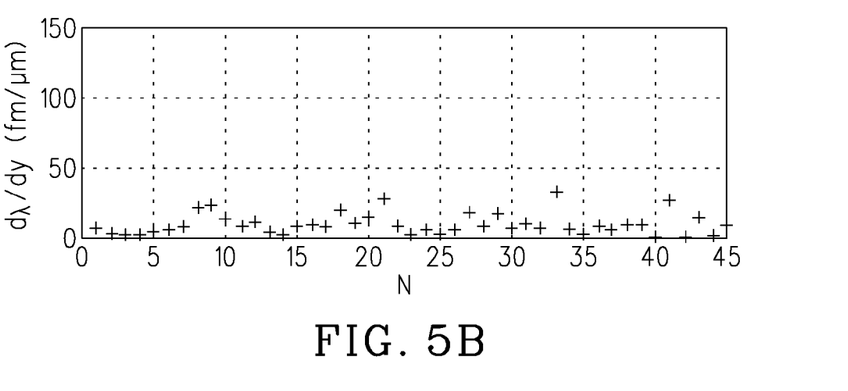
Figure 5C:
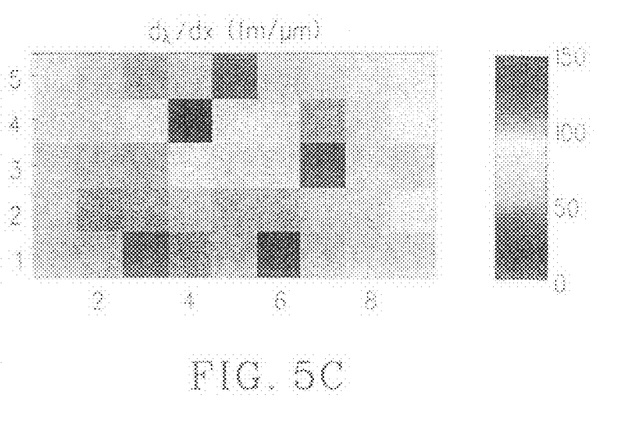
Figure 5D:
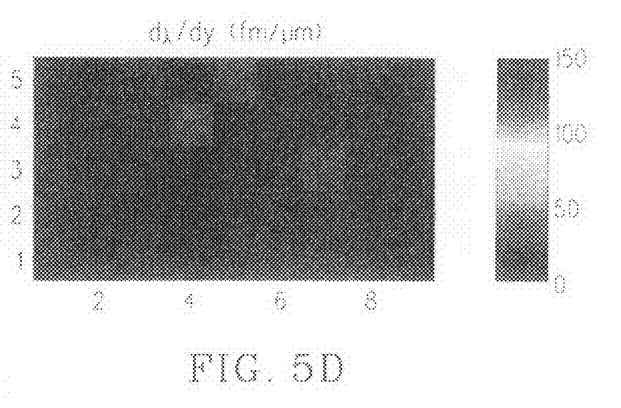

The source/detector noise was measured by monitoring the difference between the centroids of the sample and reference regions 202 and 204 of a given biosensor 102. In FIG. 4 there is a graph illustrating a sample of the data (100 points) that where collected which showed a 1 sigma value of ~16 fm. The data collection time for each point was ~1 second. Similar noise values where also seen for the other biosensors 102b . . . 102n as long as the optical beam 138b . . . 138n was within 0.5 mm of the center of their respective wells 122 (and biosensors 102b . . . 102n) within the microplate 124.

II. Translational Sensitivity

The translation sensitivity was measured over a 5×9 grid of 45 wells 122 in the microplate 124 where each well 122 had their x and y translational dependence respectively measured. In addition, the translation measurements included measuring the (referenced) centroid at 21 equally spaced locations spanning a length of 100 μm. For each well 122, a linear fit was made to this data and then the slope of these lines where found for the x and y directions. The results of this experiment are shown in FIGS. 5A-5D. In particular, the translation measurement results for the x and y directions are respectively shown in FIGS. 5A and 5B. And, the spatial dependence of the translational variations in the x and y direction's are respectively shown in FIGS. 5C and 5D. In viewing FIGS. 5A-5D, it can be seen that the translational sensitivity is about 50-100 fm/μm or less in the x-direction and is only about 10-20 fm/μm in the y-direction. The values in the y-direction are basically at the noise limit of the experimental defocused dual optical interrogation system 100.

Figure 6A:
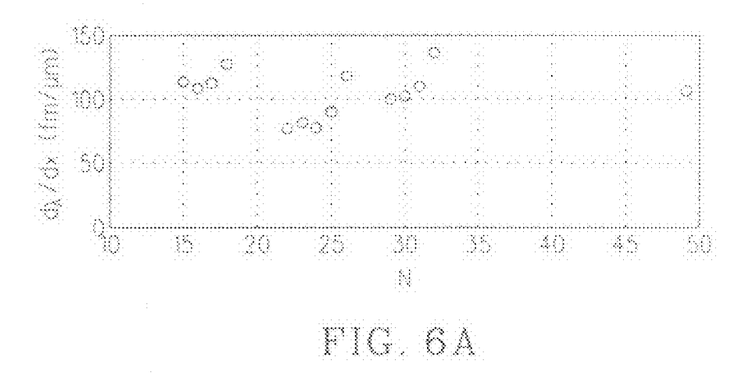
Figure 6B:
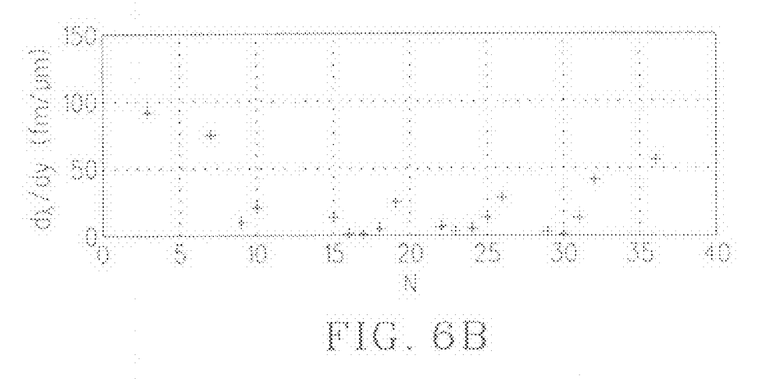
Figure 6C:
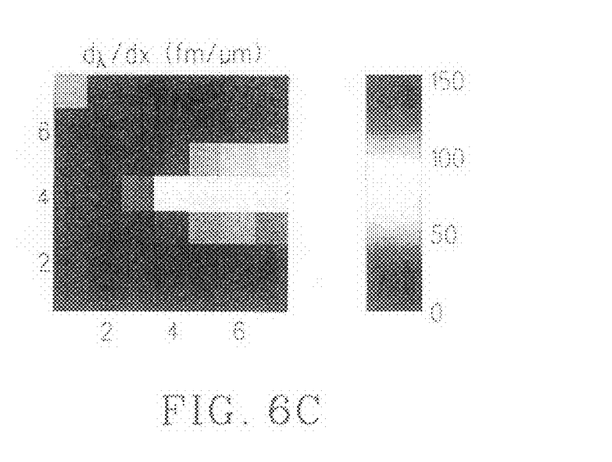
Figure 6D:
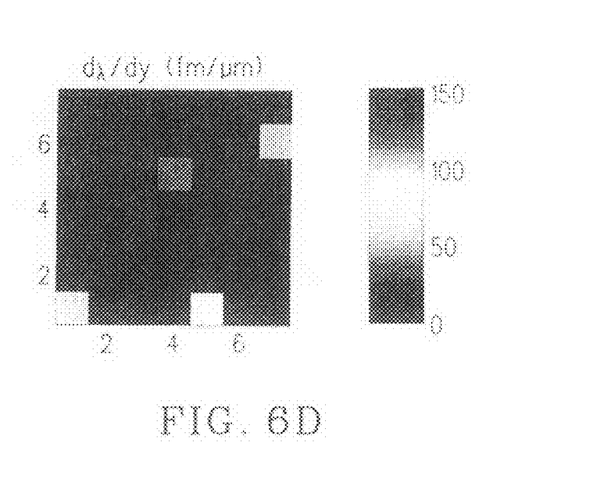

Next, the translational sensitivity associated with a single well 122 (biosensor 102a) of the microplate 124 was examined. The translational sensitivity was measured on a 7×7 grid within a single well 122 (biosensor 102a) covering an area of 1.5 mm square. The translational measurement results for all 49 data points in the x-direction and y-direction are respectively shown in FIGS. 6A and 6B. And, the spatial dependence of the translational sensitivity in the x-direction and y-direction within the 1.5 mm region of the well 122 (biosensor 102a) are respectively shown in FIGS. 6C-6D (note: that in these two figures any point that was measured higher than 150 fm/μ was plotted as equal to this value).

In viewing FIGS. 6A-6D, it can be seen that the lateral sensitivity in the x direction was about 70 fm/μm or greater while the lateral sensitivity was about 20 fm/μm in the y-direction. One possible contributing factor for this dependency is the fact that for translation in the x-direction, the sizes of the signal and reference regions 202 and 204 are altered by the x-translation of the microplate 20. In other words, as the microplate 124 is moved in the +x direction then the signal region 202 (for example) will increase in size as the reference region 204 decreases in size. Of course, the opposite is true for x translation in the reverse direction. Therefore, variations in the resonance wavelength across the well 122 (biosensor 102a) adversely contributed to the lateral sensitivity. This is most likely the largest contributor to the lateral sensitivity which accounts for why the dependency in the x-direction is greater than it is in the y-direction. The small dependence in the y-direction is possibly a result of the fact that the optical beam 138a is not perfectly uniform over the well 122 (biosensor 102a) within the microplate 124. This would cause a different power weighting to be applied to the resonance (assuming the sensor resonant wavelength is not spatially uniform) which gives rise to a small amount of y-direction (and also x-direction) lateral dependency. For y translations, the sizes of the reference and signal regions 202 and 204 are not altered.

Figure 7A:
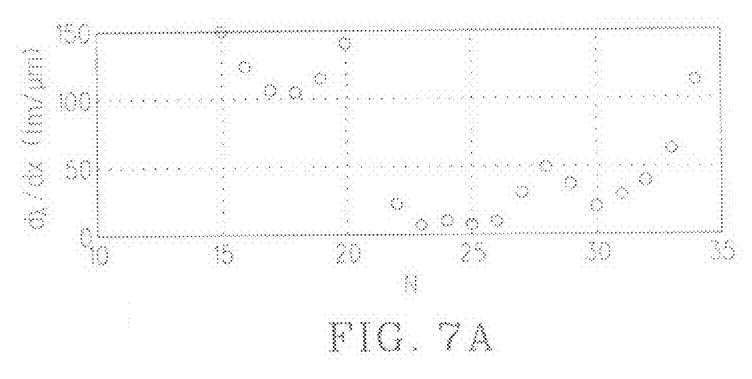
Figure 7B:
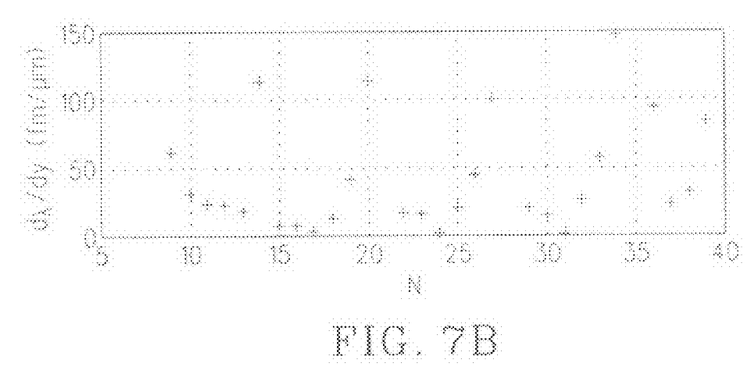
Figure 7C:
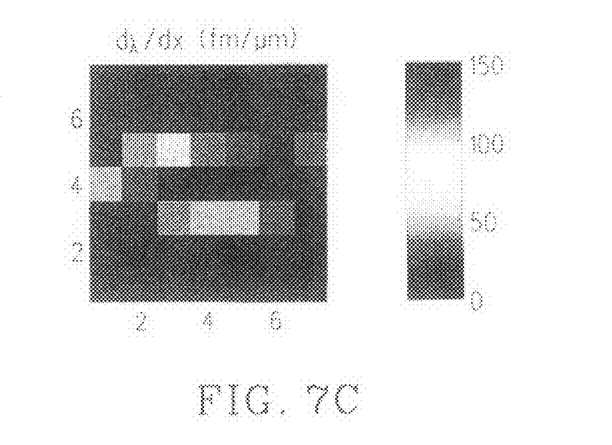
Figure 7D:
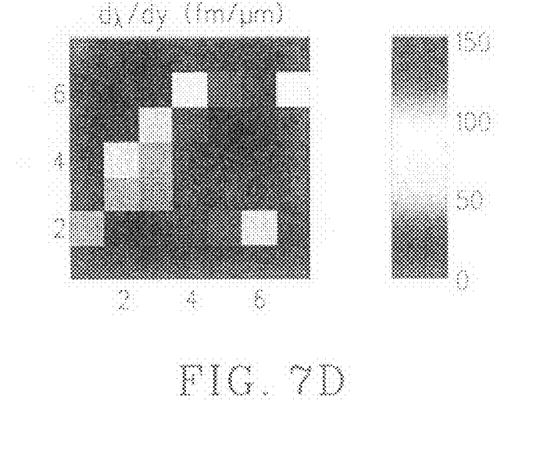
Figure 7E:
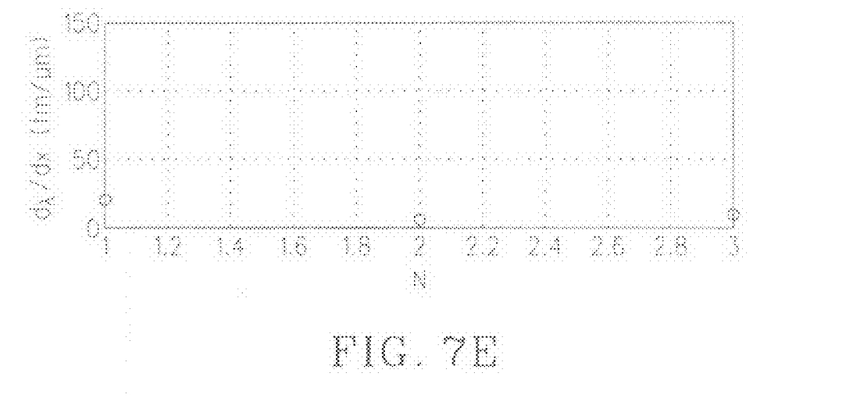
Figure 7F:
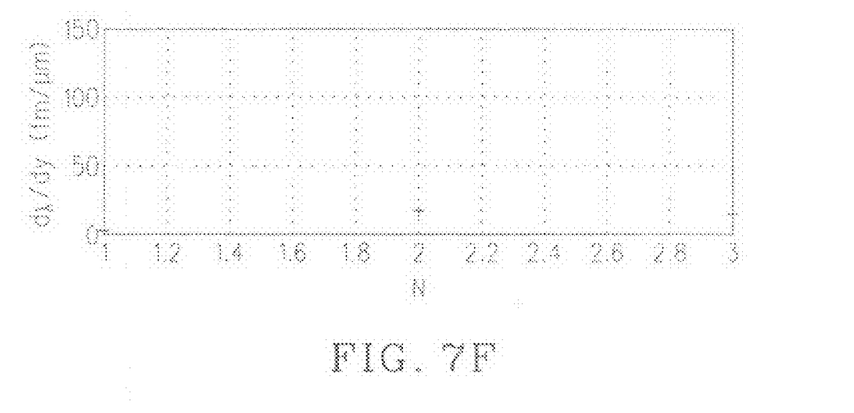

A modification was made to the biosensors 102a, 102b ... 102n in an attempt to reduce the lateral (and angular, see next section) dependency. In particular, opaque strips/masks 210 (in this case 400 μm diameter wires) where placed within the wells 122 to divide the individual biosensors 102a, 102b ... 102n into two equal signal and reference regions 202 and 204. Because of the 400 μm wide opaque strips/masks 210 on the biosensors 102a, 102b ... 102n, the size of the signal and reference regions 202 and 204 would not change as the microplate 124 was moved in the x-direction for translations up to 400 μm length. With the modified biosensors 102a, 102b ... 102n, the lateral sensitivity in the x-direction and the y-direction within a single masked well 122 and three masked wells 122 where measured (in the same manner as was done above) and the results have been displayed in FIGS. 7A-7F. In particular, the translational measurement results for all 49 data points in the x-direction and y-direction of the single well 122 (having the masked biosensor 102) are respectively shown in FIGS. 7A and 7B (note: of these 49 measured points, only those with sensitivities less than 150 fm/um are shown in FIGS. 7A and 7B) And, the spatial dependence of the translational sensitivity in the x-direction and y-direction within the 1.5 mm region of the single well 122 (having the masked biosensor 102) are respectively shown in FIGS. 7C-7D (note: that in these two figures any point that was measured higher than 150 fm/μ was plotted as equal to this value). As can be seen, with the masked biosensor 102 the lateral sensitivity had been significantly improved to be approximately 20 fm/μm in both the x-direction and the y-direction. Finally, the lateral sensitivity was measured across three wells 122 (with three masked biosensors 102) and the translational sensitivity in the x-direction and y-direction for these three wells 122 have been respectively shown in FIGS. 7E and 7F.

III. Angular Sensitivity

The microplate holder used in the angular sensitivity test was equipped with manual controls for tilting the microplate 124 about the x- and y-axes. For the measurements of the angular sensitivity, the microplate 124 was rotated in increments of 1 mRad. Finer increments would have been desirable since the one sigma error on plate tilt was expected to be ~12 μRad. Nonetheless, the angular sensitivity did not show a dramatic change within these relatively coarse adjustments, so it was reasonable to extrapolate these results to the small tilt angles that would likely be encountered in an operational defocused dual optical interrogation system 100. In this experiment, two sets of angular sensitivity measurements were made: one for the microplate 124 without the opaque masked (wire) wells 122 (biosensors 102) and one where the microplate 124 had the opaque masked (wire) wells 122 (masked biosensors 102).

Figure 8A:
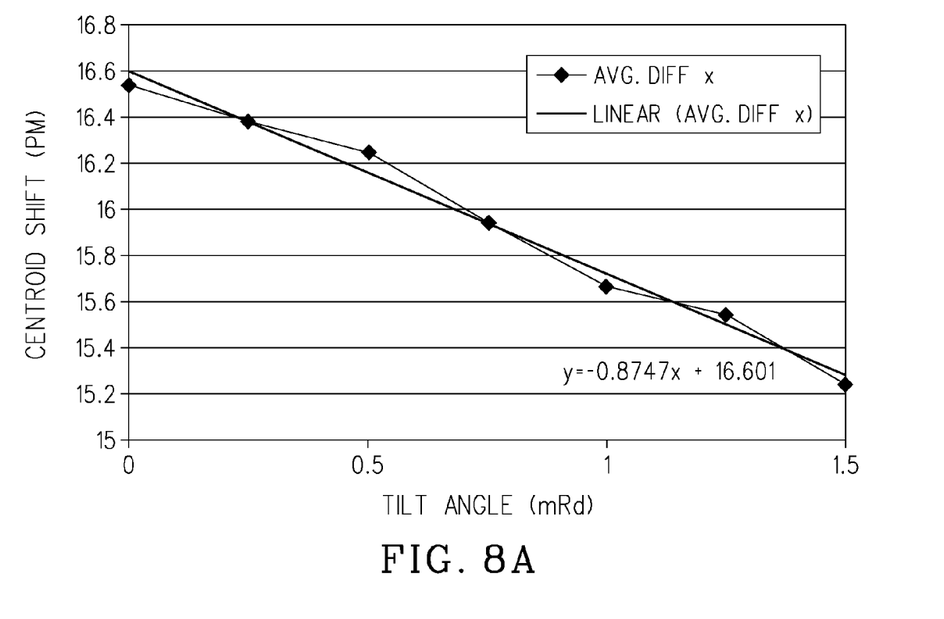
Figure 8B:
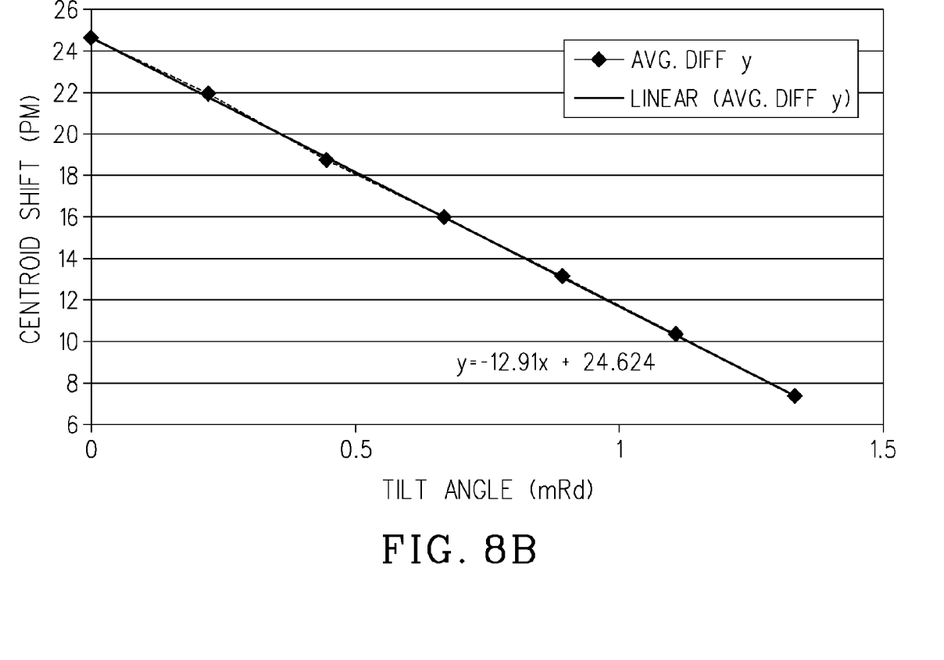

For the microplate 124 without the mask, the measured dependencies for tilt in the x- and y-axes are respectively shown in FIGS. 8A and 8B. In viewing FIGS. 8A and 8B, it can be seen that the slopes of the curves in the graphs indicate that the angular sensitivity is about 1 fm/μRad for tilt about the x-axis and 13 fm/μRad for tilt about the y-axis. This higher dependence about the y-axis was expected since this tilt shifts the size of the signal and reference regions 202 and 204 (in a similar manner as was described for the x-lateral translation measurements). Since, the tilt variation is expected to be 12 μRd (one sigma), this implies a tilt sensitivity of 12 fm about the x-axis, and a much higher sensitivity of 156 fm about the y-axis of an operational defocused dual optical interrogation system 100.

Figure 9A:
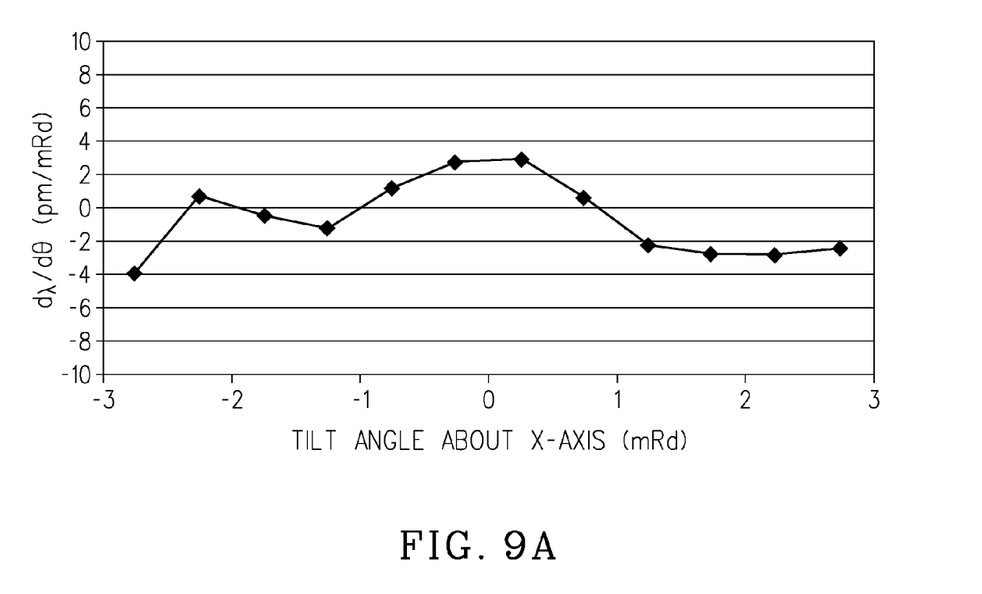
Figure 9B:
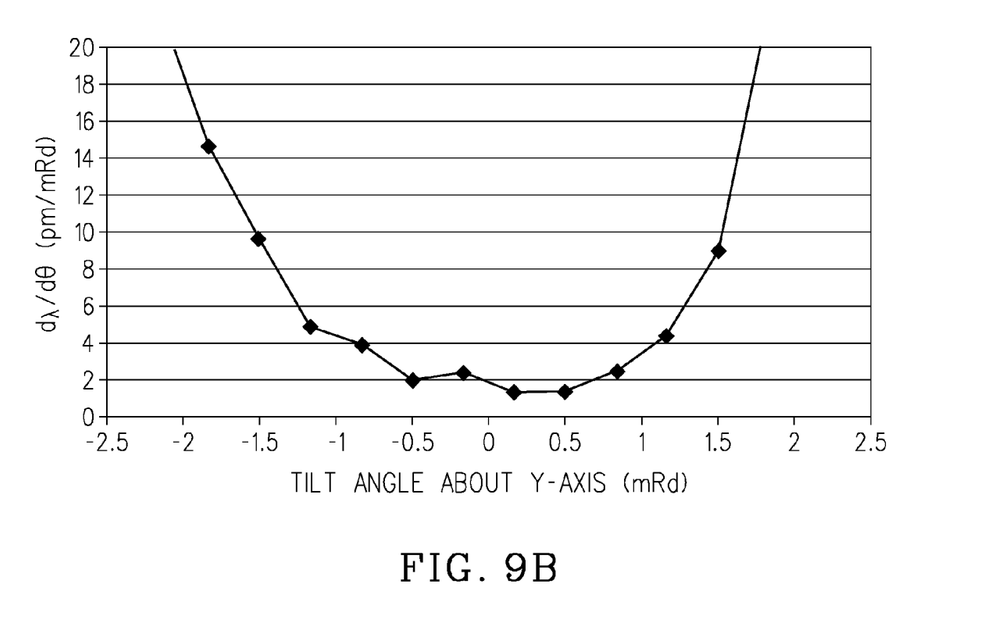

Next, the angular sensitivity measurements were repeated for the microplate 124 with the 400 um masked wells 122 (masked biosensors 102). The measured dependencies for tilt in the x- and y-axes for this case have been, respectively shown in FIGS. 9A and 9B. For this case, it can be seen that the angular sensitivity was about 2 fm/μRad for tilt about the x-axis and about 2 fm/μRad for tilt about the y-axis. This lower dependence about the y-axis (over a 2 mRad range) was expected since the mask 210 on the biosensor 102 maintained the size (and location) of the signal and reference regions 202 and 204 while tilting the microplate 124. Thus, for this configuration and using the expected tilt variation of 12 μRd implies that the tilt sensitivity would be only 24 fm about either the x-axis or y-axis for an operational defocused dual optical interrogation system 100.

IV. Parasitic Fringes

Multiple reflections within the microplate 124 (which in these tests happened to be 0.7 mm thick) gave rise to fringes which had an ~0.3 nm period in the resulting resonance spectrum. These fringes can be problematical since they could bias the perceived resonance peak. For the results that have been presented herein, these fringes have been removed in software (by convolving the measured resonance with a 400 pm wide gaussian) prior to performing any sort of analysis. This software filtering technique is applicable here since the width of the resonance was sufficiently wide compared with the period of these parasitic fringes. However, if an operational defocused dual optical interrogation system 100 is used then a digital filtering technique could be used to remove parasitic interference fringes before the final computation of centroid wavelengths. Examples of several digital filtering techniques where discussed in the co-assigned U.S. Patent Application No. 60/781,397 filed on Mar. 10, 2006 and entitled "Optimized Method for LID Biosensor Resonance Detection". The contents of this document are hereby incorporated by reference herein.

V. Wavelength Noise

The wavelength noise affects the accuracy with which the wavelengths of the data points can be measured. The value of this particular wavelength uncertainty was not measured in these experiments since the contribution that this noise/error makes to the measurement has already been taken into account in the source/detector noise measurement tests. Plus, the wavelength noise has been estimated to be below 50 fm.

Experimental Conclusions

The experimental defocused dual optical interrogation system 100 described herein has been evaluated for various performance parameters including, source/detector noise, translational/lateral sensitivity and angular sensitivity. A modification to the biosensors 102a, 102b ... 102n in which a mask 210 has been employed yielded improved performance of the experimental defocused dual optical interrogation system 100. A brief summary of these results are provided in TABLE 1:

TABLE 1

| | Dual Detector Optical Interrogation System 100 |
|---|---|
| Source/Detector noise | 16 fm |
| Lateral sensitivity | 25 fm/μm |
| Angular sensitivity | 2 fm/μRad |

Figure 10:
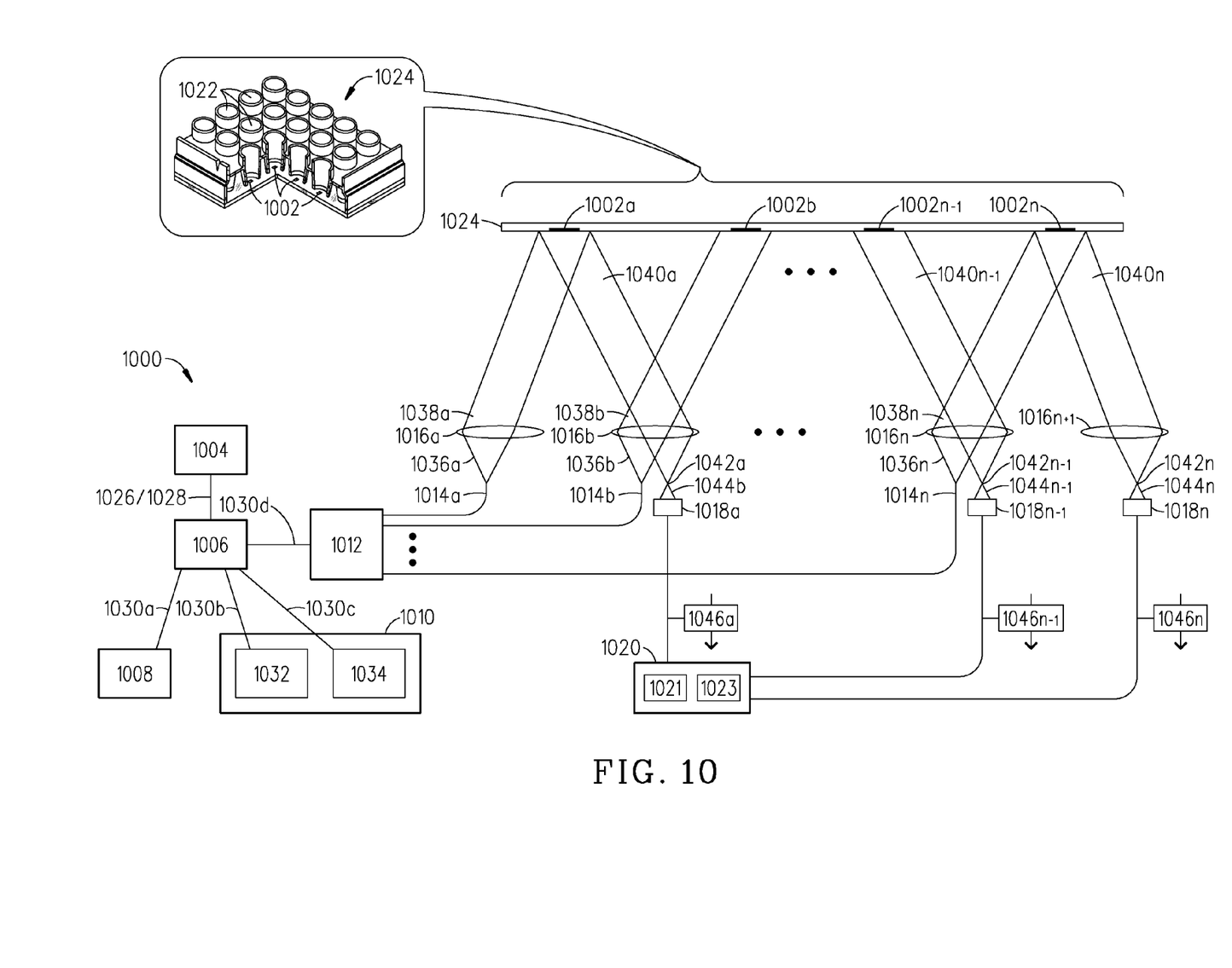
FIG. 10 is a block diagram of an exemplary optical interrogation system which is configured to interrogate one or more biosensors in accordance with a second embodiment of the present invention.

Referring to FIG. 10, there is a block diagram illustrating the basic components of an exemplary optical interrogation system 1000 which is configured to interrogate one or more biosensors 1002a, 1002b . . . 1002n in accordance with a second embodiment of the present invention. The exemplary optical interrogation system 1000 includes a tunable laser 1004, a 1×4 splitter 1006, a power tracking device 1008, a wavelength tracking device 1010, a 1×N splitter 1012, N-fiber launches 1014a, 1014b . . . 1014n (e.g., N-single mode optical fibers 1014a, 1014b . . . 1014n), N+1 lenses 1016a, 1016b . . . 1016n, 1016n+1 (e.g., N+1 doublets 1016a, 1016b . . . 1016n, 1016n+1) and N-detectors 1018a, 1018b . . . 1018n (e.g., N-dual detectors 1018a, 1018b . . . 1018n) and a data processing device 1020 (e.g., computer 1020). In this example, the biosensors 1002a, 1002b . . . 1002n are shown located within the wells 1022 of a microplate 1024 (note: the microplate 1024 can have any number of wells 1022 such as for example 96-wells, 384-wells and 1536-wells). For a detailed discussion about an exemplary microplate 1024, reference is made to the co-assigned U.S. patent application Service Ser. No. 11/489,173 (the contents of which are incorporated by reference herein).

The tunable laser 1004 (e.g., swept wavelength tunable laser 1004) emits an optical beam 1026 which has a predetermined sequence of distinct wavelengths over a predetermined time period. For instance, the tunable laser 1004 can have a tuning range where the emitted optical beam 1026 sequences through 840 nm to 852 nm at 12 nm increments without mode hop at a tuning speed of 0.1 nm/sec to 300 nm/sec. The tunable laser 1004 is shown emitting the optical beam 1026 into a fiber optic cable 1028 which is connected to the 1×4 splitter 1006. In this example, the 1×4 splitter 1006 receives the optical beam 1026 and inputs the optical beam 1026 into four separate fiber optic cables 1030a, 1030b, 1030c and 1030d.

The first fiber optic cable 1030a interfaces with the power tracking device 1008 which functions to track the changing power of the optical beam 1026 emitted from the tunable laser 1004 (note: the power of the tunable laser 1004 varies as it changes the wavelength of the optical beam 1026). The power tracking device 1008 monitors this changing power which is used by the data processing device 1020 as a power reference to remove the effect of power variations in the output of the spectra from the interrogated biosensor(s) 1002a, 1002b . . . 1002n.

The second and third fiber optic cables 1030b and 1030c interface with the wavelength tracking device 1010 which functions to track the changing wavelengths of the optical beam 1026 emitted from the tunable laser 1004. In one embodiment, the wavelength tracking device 1010 includes a fiber Mach-Zehnder interferometer 1032 and an athermalized etalon 1034. The fiber Mach-Zehnder interferometer 1032 is used to decode the instantaneous wavelength of the optical beam 1026 to a very high resolution while operating the tunable laser 1004. The athermalized etalon 1034 is used to provide an accurate reference of the wavelength of the optical beam 1026 while operating the tunable laser 1004. An alternative embodiment for tracking the changing wavelengths of the optical beam 1026 that could also be used herein was discussed in the co-assigned U.S. patent application Ser. No. 11/711,207—the contents of which are hereby incorporated by reference herein).

The fourth fiber optic cable 1030d interfaces with the 1×N splitter 1012 which interfaces with N-fiber launches 1014a, 1014b . . . 1014n (e.g., N single-mode fibers 1014a, 1014b . . . 1014n) where each fiber launch 1014a, 1014b . . . 1014n outputs an optical beam 1036a, 1036b . . . 1036n towards a corresponding collimating/imaging lens 1016a, 1016b . . . 1016n (note: the last lens 1016n+1 is not coupled with a fiber launch 1014)). The lenses 1016a, 1016b . . . 1016n respectively collimate the optical beams 1036a, 11036b . . . 1036n and direct the collimated optical beams 1038a, 1038b . . . 1038n to illuminate and preferably overfill the corresponding biosensors 1002a, 1002b . . . 002n. The adjacent lenses 1016b, 1016c . . . 1016n+1 receive the optical beams 1040a, 1040b . . . 1040n that are respectively reflected from the corresponding biosensors 1002a, 1002b . . . 1002n (note: this configuration is different than the optical interrogation system 100 shown in FIG. 1 where the lenses 116a, 116b . . . 116n respectively receive the optical beams 140a, 140b . . . 140n that are reflected from the corresponding biosensors 102a, 102b . . . 102n). Then, the adjacent lenses 1016b, 1016c . . . 1016n+1 focus the corresponding reflected optical beams 10140a, 1040b . . . 1040n which are then allowed to diverge beyond the focal points 1042a, 1042b . . . 1042n of the adjacent lenses 1016b, 1016c . . . 116n+1 so the optical beams 1044a, 1044b . . . 1044n form an image of the biosensors 1002a, 1002b . . . 1002n at an image plane upon the corresponding detectors 1018a, 1018b . . . 1018n (e.g., dual detectors 1018a, 1018b . . . 1018n can be used to receive the sample spectra and reference spectra from corresponding biosensors 1002a, 1002b . . . 1002n). Alternatively, the detectors 1018a, 1018b . . . 1018n can be positioned ahead or before the focal points 1042a, 1042b . . . 1042n and not at the image plane and in this particular configuration the detectors 1018a, 1018b . . . 1018n would still receive images of the biosensors 1002a, 1002b . . . 1002n.

The detectors 1018a, 1018b . . . 1018n generate a sequence of images 1046a, 1046b . . . 1046n of the respective biosensors 1002a, 1002b . . . 1002n where each of the images 1046a, 1046b . . . 1046n corresponds with one of the distinct wavelengths of the optical beam 1026 that was emitted from the tunable laser 1004. For instance, detector 1018a generates a sequence of images 1046a of the illuminated biosensor 1002a where each image 1046a corresponds with one of the distinct wavelengths of the optical beam 1026 (and optical beam 1036a) that was emitted from the tunable laser 1004 (and the fiber launch 1014a). Lastly, the data processing device 1026 (e.g., computer 1026) receives the collected images 1046a, 1046b . . . 1046n and has a processor 1021 which uses instructions accessed from memory 1023 to process the collected images 1046a, 1046b . . . 1046n to determine, for example whether or not there was a biochemical interaction or some other event that occurred on one or more of the biosensors 1002a, 1002b . . . 1002n.

The exemplary optical interrogation system 1000 has a configuration that is desirable since it effectively solves a problem where it is now possible to collect the optical signals 1040a, 1040b . . . 1040n from individual biosensors 1002a, 1002b . . . 1002n in the microplate 1024 while enabling the detectors 1018a, 1018b . . . 1018n and the corresponding fiber launches 1014a, 1014b . . . 1014n to be positioned relatively close enough to one another. In the past, this was a problem because the physical geometry and placement of the fiber launches and detectors would dictate the minimum separation possible. One potential solution to this problem involved increasing the angle of incidence of the optical beams that were directed to the biosensors. However, the angle of incidence can only be increased to a point, otherwise vignetting will occur thereby compromising performance. The optical interrogation system 1000 of the present invention effectively addresses this problem because it's configuration allows one to obtain a large separation between each pair of fiber launches 1014a, 1014b . . . 1014n and the detectors 1018a, 1018b . . . 1018n thus one can increase the angle of incidence of the optical beams 1036a, 1036b . . . 1036n and avoid the problematical vingetting by emitting the optical beams 1038a, 1038b . . . 1038n from one lens 1016a, 1016b . . . 1016n and then collecting the reflected light 1040a, 1040b . . . 1040n with the corresponding adjacent lens 1016b, 1016c . . . 1016n+1 (see FIG. 10). In addition, the reflected optical beams 1040a, 1040b . . . 1040n can be detected away from both the launch plane and image plane or at the image plane by the corresponding detectors 1018a, 1018b . . . 1018n. However, there are several advantages for detecting at the image plane which are: (1) the spot location does not shift with the tilt (or bow) of the microplate 1024 therefore, this setup is insensitive to this parameter; and (2) the detectors 1018a, 1018b . . . 1018n are located at a different plane than the fiber launches 1014a, 1014b . . . 1014n thereby allowing more space for the detectors 1018a, 1018b . . . 1018n. For example, the vertical distance between the fiber launches 1014a, 1014b . . . 1014n and image planes can be 7 mm, between the fiber launches 1014a, 1014b . . . 1014n and lenses 1016a, 1016b . . . 1016n can be 18 mm and between the lenses 1016a, 1016b . . . 1016n and the microplate 1024 can be 65 mm.

In comparing the optical interrogation system 100 and the optical interrogation system 1000 it should be noted that in the configuration of the optical interrogation system 100 the lenses 116a, 116b . . . 116n do not form a (real) image (in the classical sense) of the biosensors 102a, 102b . . . 102n for any placement location of the detectors 118a, 118b . . . 118n. In other words, the optical interrogation system 100 does not have an image plane beneath the lenses 116a, 116b . . . 116n that corresponds to the biosensors 102a, 102b . . . 102n above the lenses 116a, 116b . . . 116n. However, it is true at various locations of the detectors 118a, 118b . . . 118n either ahead of or past the focal points 142a, 142b . . . 142n of the lenses 116a, 116b . . . 116n that the detectors 118a, 118b . . . 118n can still "see" the biosensors 102a, 102b . . . 102b (but not right at the focal points 142a, 142b . . . 142n of the lenses 116a, 116b . . . 116n). This is because the optical interrogation system 100 has a large "depth of focus" which is a result of the fact that there is only collimated light 140a, 140b . . . 140n being reflected from the biosensors 102a, . . . 102n.

In contrast, the optical interrogation system 1000 has a distance between the lenses 1016a, 1016b . . . 1016n, 1016n+1 and the microplate 1024 that is significantly larger than in the optical interrogation system 100.

Because of this increased distance the detectors 1018a, 1018b . . . 1018n can be located at the image plane, that is, the biosensors 1002a, 1002b . . . 1002n can be imaged onto the detectors 1018a, 1018b . . . 1018n. Again, it should be appreciated that the detectors 1018a, 1018b . . . 1018n could be positioned ahead of or after the image plane and still give a workable system (as long as the detectors 1018a, 1018b . . . 1018n are not located at the focal points 1042a, 1042b . . . 1042n). However, placing the detectors 1018a, 1018b . . . 1018n at the image plane is preferred since it results in an optical interrogation system 1000 that is insensitive to the curvature of the microplate 1024. In addition, it should be appreciated that if one were to build the optical interrogation system 100 then they could create the optical interrogation system 1000 by adding lens 1016n+1 (and a detector 1018n to receive the light 1040n from this lens 1016n+1) and by moving the microplate 1024 "up" and "to the right" (compare FIGS. 1 and 10).

Although two embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

The invention claimed is:

1. An optical interrogation system comprising:
   a tunable laser for emitting an optical beam;
   a first fiber launch for receiving the optical beam emitted from said tunable laser and then outputting a first optical beam;
   a first lens for collimating the first optical beam outputted from said first fiber launch such that the collimated first optical beam illuminates a first biosensor;
   a second lens for receiving a first reflected optical beam from the first biosensor;
   a first detector for receiving the first reflected optical beam from said second lens;
   a data processing device for receiving one or more images associated with the first reflected optical beam received at said first detector;
   a second fiber launch for receiving the optical beam generated by said tunable laser and then outputting a second optical beam;
   said second lens for collimating the second optical beam outputted from said second fiber launch such that the collimated second optical beam illuminates a second biosensor;
   a third lens for receiving a second reflected optical beam from the second biosensor;
   a second detector for receiving the second reflected optical beam from said third lens; and
   said data processing device for receiving one or more images associated with the second reflected optical beam received at said second detector.

2. The optical interrogation system of claim 1, wherein said first detector is located ahead or past a focal point of said second lens.

3. The optical interrogation system of claim 1, wherein the second lens is a second doublet lens.

4. The optical interrogation system of claim 3, wherein the second doublet lens has at least a portion of the first reflected optical beam received from the first biosensor overlap therein with at least a portion of the second collimated optical beam which illuminates the second biosensor.

5. The optical interrogation system of claim 1, further comprising a wavelength tracking device which tracks the distinct wavelengths of the optical beam generated by said tunable laser.

6. The optical interrogation system of claim 1, further comprising a power tracking device which receives the optical beam generated by said tunable laser and tracks the power of said tunable laser.

7. The optical interrogation system of claim 1, wherein said data processing device further processes the one or more intensity spot patterns to determine whether or not there was a biochemical interaction on the biosensor.

8. The optical interrogation system of claim 1, wherein:
said first biosensor is located within a first well of a microplate; and
said first biosensor has a mask located on a surface thereon to separate a signal region from a reference region.

9. A method for interrogating one or more biosensors, said method comprising the steps of:
   emitting a first optical beam which has a predetermined sequence of distinct wavelengths over a predetermined time period;
   using a first lens to collimate the first optical beam such that the first collimated optical beam illuminates a first biosensor;
   using a second lens to receive a first reflected optical beam from the first biosensor;
   using a first detector to receive the first reflected optical beam from said second lens;
   using a data processing device to receive a plurality of images associated with the first reflected optical beam that was received at said first detector where each image corresponds with one of the distinct wavelengths of the first emitted optical beam;
   emitting a second optical beam which has a predetermined sequence of distinct wavelengths over a predetermined time period;
   using said second lens to collimate the second optical beam such that the second collimated optical beam illuminates a second biosensor;
   using a third lens to receive a second reflected optical beam from the second biosensor;
   using a second detector to receive the second reflected optical beam from said third lens; and
   using a data processing device to receive a plurality of images associated with the second reflected optical beam that was received at said second detector where each image corresponds with one of the distinct wavelengths of the second emitted optical beam.

10. The method of claim 9, wherein said first detector is located ahead or past a focal point of said second lens.

11. The method of claim 9, wherein the second lens is a second doublet lens.

12. The method of claim 11, wherein the second doublet lens has at least a portion of the first reflected optical beam received from the first biosensor overlap therein with at least a portion of the second collimated optical beam which illuminates the second biosensor.

13. The method of claim 9, further comprising a step of tracking the distinct wavelengths of the first emitted optical beam.

14. The method of claim 9, further comprising a step of tracking the power of a tunable laser which generated the first emitted optical beam.

15. The method of claim 9, further comprising a step of using the data processing device to process the intensity spot patterns to determine whether or not there was a biochemical interaction on the first biosensor.

16. The method of claim 9, wherein:
said first biosensor is located within a first well of a microplate; and
said first biosensor has a mask located on a surface thereon to separate a signal region from a reference region.

\* \* \* \* \*